US008870102B2

(12) United States Patent
O'Dea et al.

(10) Patent No.: US 8,870,102 B2
(45) Date of Patent: Oct. 28, 2014

(54) ELECTROSPRAYING DEVICES AND METHODS

(75) Inventors: Shirley O'Dea, County Kildare (IE); Michael Maguire, Dublin (IE)

(73) Assignee: NationalUniversity of Ireland, Maynooth, Maynooth, County Kildare (IE)

( * ) Notice: Subject to any disclaimer, the term of this patent is extended or adjusted under 35 U.S.C. 154(b) by 812 days.

(21) Appl. No.: 12/989,102

(22) PCT Filed: Apr. 20, 2009

(86) PCT No.: PCT/EP2009/054680

§ 371 (c)(1),
(2), (4) Date: Oct. 22, 2010

(87) PCT Pub. No.: WO2009/130187

PCT Pub. Date: Oct. 29, 2009

(65) Prior Publication Data

US 2011/0040147 A1 Feb. 17, 2011

(30) Foreign Application Priority Data

Apr. 22, 2008 (IE) .................................. S2008/0310

(51) Int. Cl.
*B05B 5/00* (2006.01)
*A61M 1/00* (2006.01)

(Continued)

(52) U.S. Cl.
CPC ................ *A61M 15/02* (2013.01); *B05B 9/042* (2013.01); *B05B 1/32* (2013.01); *A61M 16/0477* (2013.01); *B05B 1/14* (2013.01); *B05B 1/30* (2013.01); *B05B 5/0255* (2013.01); *B05B 5/16* (2013.01)
USPC ............................................ 239/690; 604/30

(58) Field of Classification Search
CPC ............. F16K 7/06; F16K 7/08; F16K 7/068; F16K 7/07; F16K 7/075; F16K 7/065; F16K 7/061; F16K 7/063; A61M 2039/1027; A61M 39/12; A61M 39/288; A61M 39/0613; A61M 39/286; A61M 39/28; A61M 39/283; A61M 39/284; A61M 11/00–11/08; A61M 3/0275; B05B 5/1691; B05B 5/0255; B05B 5/043; B05B 5/0533; B05B 5/053; B05B 5/047; B05B 5/0531; B05B 5/032; B05B 12/14; B05B 5/0403; B05B 5/03; B05B 1/306; B05B 5/025; B05B 5/0407; B05B 7/0815; B05B 5/0418
USPC ............................................ 239/690; 604/30
See application file for complete search history.

(56) References Cited

U.S. PATENT DOCUMENTS 2,300,679 A * 11/1942 Klein ........................... 239/455
2,590,215 A * 3/1952 Sausa ............................ 138/45

(Continued)

FOREIGN PATENT DOCUMENTS

| | | |
|---|---|---|
| DE | 101 29 250 | 6/2002 |
| WO | WO 2004/078244 | 9/2004 |

OTHER PUBLICATIONS

Stark et al., WO 2007/066122A1, date of publication: 2007.*

(Continued)

*Primary Examiner* — Manuel Mendez
(74) *Attorney, Agent, or Firm* — Whiteford, Taylor & Preston, LLP; Gregory M. Stone

(57) ABSTRACT

An electrospray head for use in an electrospraying apparatus comprises a body with an internal surface defining a conduit having an inlet for receiving a fluid to be sprayed and an outlet for emitting the fluid. A movable wall forms a part of the internal surface defining the conduit, the movable wall being arranged to constrict or dilate the conduit upon operation of the actuator. The movable wall can thus control the delivery of fluid through the outlet from the conduit.

28 Claims, 6 Drawing Sheets

(51) Int. Cl.**
*A61M 15/02* (2006.01)
*B05B 9/04* (2006.01)
*B05B 1/32* (2006.01)
*A61M 16/04* (2006.01)
*B05B 1/30* (2006.01)
*B05B 5/025* (2006.01)
*B05B 5/16* (2006.01)
*B05B 1/14* (2006.01)

(56) References Cited

U.S. PATENT DOCUMENTS

| | | | | |
|---|---|---|---|---|
| 2,627,874 A | * | 2/1953 | Johnson | 251/5 |
| 2,633,154 A | * | 3/1953 | Eastman | 251/5 |
| 2,756,959 A | * | 7/1956 | Hill | 251/5 |
| 5,056,720 A | * | 10/1991 | Crum et al. | 239/698 |
| 5,505,706 A | * | 4/1996 | Maus et al. | 604/131 |
| 5,813,454 A | * | 9/1998 | Potter | 165/276 |
| 5,820,542 A | * | 10/1998 | Dobak et al. | 600/16 |
| 6,135,369 A | * | 10/2000 | Prendergast et al. | 239/690 |
| 6,216,966 B1 | * | 4/2001 | Prendergast et al. | 239/690 |
| 6,252,129 B1 | * | 6/2001 | Coffee | 602/42 |
| 6,764,720 B2 | * | 7/2004 | Pui et al. | 427/479 |
| 7,152,817 B2 | | 12/2006 | Wilson et al. | |
| 7,258,285 B1 | * | 8/2007 | Combs et al. | 239/546 |
| 8,034,065 B2 | * | 10/2011 | Coe et al. | 606/157 |
| 2003/0205631 A1 | | 11/2003 | Barron et al. | |
| 2009/0266924 A1 | * | 10/2009 | Pui et al. | 239/696 |

OTHER PUBLICATIONS

Mamanee, W. et al., "PDMS Based Thermopneumatic Peristaltic Micropump for Microfluidic Systems." Journal of Physics: Conference Series, Institute of Physics Publishing, Bristol, GB. vol. 34, No. 1, Apr. 1, 2006. pp. 564-569.

* cited by examiner

ELECTROSPRAYING DEVICES AND METHODS

TECHNICAL FIELD

This invention relates to the field of electrospraying, in particular to improved electrospraying devices and methods.

BACKGROUND ART

Electrospraying employs electrostatic repulsion and acceleration resulting from a high voltage to create an aerosol or plume of droplets. Typically, the droplets will be a volatile solvent in which a molecule, ion or particle of interest is suspended or dissolved.

Evaporation of the solvent from the drop surface causes the space charge effects on an ever-decreasing droplet to make the droplet unstable, disintegrating into smaller, highly charged droplets, which can disintegrate entirely due to the high charge concentration.

A typical electrospray system will comprise, at its most basic:
- a liquid supply source,
- a capillary, needle, nozzle, or other delivery orifice leading from the liquid supply source,
- a high voltage electrical source for applying a strong electric field to the liquid emerging from the open end of the delivery tube, and
- a counter-electrode, which may be any surface to which the droplets are attracted (thus while the counter-electrode forms part of the electrospray system, it is often not an explicit part of the apparatus, since it may be an external surface towards which the nozzle approaches).

Electrospraying finds applications in various fields, including thin film deposition processes, coating and painting processes, and mass spectroscopy. U.S. Pat. No. 6,764,720 discloses the use of electrospraying techniques for delivering drug particles into cells.

A consistent problem with electrospraying techniques is the reliable creation of an electrospray. The creation of a plume which will form an electrospray tends to be a matter of trial and error. This limits the use of the electrospray technique in any application where the liquid to be sprayed may frequently vary, since a change in the liquid properties (e.g. conductivity or viscosity) will generally mean that the parameters used to create an electrospray (source to target potential difference, liquid flow rate, nozzle dimensions) must also be varied.

The result is that one cannot easily pump a wide range of liquids through an electrospray apparatus and expect a reliable electrospray creation, since various parameters, equipment settings and even nozzles may need to be changed in order for a plume to result and an electrospray be formed.

DISCLOSURE OF THE INVENTION

The invention provides an electrospray head for use in an electrospraying apparatus, the electrospray head comprising:
- a body;
- an actuator disposed in said body;
- an internal surface in said body defining a conduit, said conduit having an inlet for receiving a fluid to be sprayed and an outlet for emitting said fluid; and
- a movable wall forming a portion of said internal surface defining the conduit;

wherein said movable wall is arranged to co-operate with said actuator to constrict or dilate said conduit upon operation of the actuator.

Conventional electrospray heads take the form of a capillary tube, needle, or other tube of fixed diameter, so the only control over the fluid dynamics in such systems for a given liquid is control over the pumping pressure applied.

By providing a movable wall which can constrict or dilate the conduit from which the liquid emerges out of the electrospray head, an additional element of control is provided to affect the fluid dynamics, and thereby one obtains an additional way of influencing the creation of the plume for an electrospray.

Preferably, the movable wall is located adjacent the outlet of the conduit whereby the effective exit diameter of the conduit can be varied by controlling the actuator.

In preferred embodiments, the movable wall comprises a cylindrical wall section whose diameter can be varied by controlling the actuator.

Preferably, said cylindrical wall section extends around the entire circumference of a cylinder.

Alternatively, said cylindrical wall section may extend around a sector of the circumference of a cylinder.

Further, preferably, said actuator is disposed circumferentially outside said cylindrical wall section.

Most preferably, said actuator is a generally cylindrical actuator operable to compress said cylindrical wall section and thereby constrict the diameter thereof.

In a preferred embodiment, the actuator comprises an expandable member disposed adjacent said movable wall, and means for varying the expansion of said expandable member.

Suitably, said expandable member comprises a fluid reservoir which may be caused to expand.

Preferably, said movable wall comprises a boundary of said reservoir.

Preferably, said fluid reservoir is constrained from movement in at least one direction, whereby the expansion of the fluid reservoir is enhanced in a different direction.

More preferably, said body is a solid structure having a seat within which said fluid reservoir is disposed.

Most preferably, said fluid reservoir is in the form of an annular cylinder having an inner cylindrical face defining said movable wall and an external cylindrical face abutting said seat in which said annular cylindrical reservoir is seated, whereby radial expansion of the reservoir is directed inwardly to constrict said inner cylindrical diameter.

Preferably, the expandable member is a thermally expandable structure, and the means for varying the expansion thereof comprises means for heating the thermally expandable structure.

Suitably, the means for heating comprises at least one resistor.

Preferably, when the fluid reservoir is in the form of an annular cylinder, the means for heating comprises a plurality of resistors disposed radially outwardly of the annular cylindrical reservoir.

In a preferred construction, the plurality of resistors are embedded in the body and flush with the seat.

The movable wall may be controllable to simultaneously constrict and dilate different portions of said conduit.

Preferably, in such cases, the movable wall is controllable to generate a peristaltic contraction movable along said conduit.

Further, preferably, said movable wall comprises a plurality of independently controllable sections which together define said conduit, and each independently controllable sec- 
tion being arranged to co-operate with an actuator to constrict or dilate a portion of said conduit upon operation of the actuator.

Optionally, the outlet of said conduit comprises a plurality of outlet orifices.

This plurality of outlet orifices may be configured to direct fluid emerging therefrom in a plurality of different directions.

Optionally, the electrospraying head further includes an electrode adapted to energise said fluid with a high voltage when connected to an appropriate power supply.

Suitably, the head may further include an electrical circuit for supplying said electrode with a high voltage.

Alternatively the electrode may be supplied from an external circuit

In a preferred embodiment, said body comprises a solid body structure having fabricated therein: said conduit; a space for receiving said movable wall; and a space for receiving said actuator.

Preferably, said solid body structure is selected from a substrate of borosilicate, quartz, or silicon.

The invention also provides an electrospraying device comprising an electrospray head as disclosed above, and means for receiving a supply of fluid for electrospraying.

A preferred implementation is a bronchoscope apparatus comprising such an electrospraying device mounted on a body adapted for insertion into the respiratory passages of a subject, whereby the electrospray head of the device may be directed at a tissue wall for delivery of an agent to said tissue by electrospraying.

Another preferred implementation is an apparatus for delivering a biological agent to a sample of cells in vitro, comprising a sample area for receiving said sample of cells, and an electrospraying device as aforesaid, the electrospraying head of said electrospraying device being positioned to deliver said biological agent from said supply of fluid to said sample of cells by electrospraying, and optionally, a counter-electrode positioned relative to the sample area to direct said electrospray.

The invention also provides a method of treatment of the human or animal body comprising the steps of providing an apparatus having an electrospray head as described herein, and operating said apparatus to deliver an electrospray agent to said human or animal body.

The invention will now be illustrated by the following description of embodiments thereof, given by way of example only with reference to the accompanying drawings, in which:

FIG. 1 is a perspective view of an electrospray head, shown from above;

FIG. 2 is a perspective view of the electrospray head of FIG. 1, shown from below;

FIG. 3 is a cross-sectional elevation of the electrospray head of FIGS. 1 and 2;

FIG. 4 is a cross-sectional elevation of a second electrospray head;

FIG. 5 is a schematic diagram of an apparatus for electrospraying a liquid, in the form of a bronchoscope;

FIG. 6 shows a laboratory or industrial system for delivering an electrospray;

FIG. 7 is a cross-sectional elevation of a third electrospray head;

FIG. 8 is a cross-sectional elevation of a fourth electrospray head;

FIG. 9 is an end elevation view of the device of FIG. 8; and

FIG. 10 is a cross-sectional elevation of a fifth electrospray head.

In FIG. 1 there is indicated, generally at 10, an electrospray head. The head has a body 12 of borosilicate glass, which has been fabricated to the desired shape, with a generally cylindrical upper section 14 and a tapering lower section 16. A central bore 18 is formed to provide a conduit for a liquid to be sprayed when supplied from a source (not shown) to which the electrospray head is connected, typically as part of an electrospray device adapted to receive the head.

Referring additionally to FIG. 2, which shows the head 10 from below, it can be seen that bore 18 extends from the upper surface 20 (FIG. 1) to the lower section 16 of the body, and that the lower section has an internal outwardly tapering surface **16*b* in addition to the external inwardly tapering surface 16*a*, these tapering faces being connected by an annular flat bottom face 22**.

As shown in FIG. 3, a coating 24 of conductive material covers the major part of the tapering surfaces **16*a*,16*b* and annular bottom face 22, and this coating 24 provides a high voltage (HV) electrode when connected to an appropriate HV source 26**.

As is generally understood in the art, and without wishing to be bound by any theory, liquid emerging from the bore 18 is exposed to an electric field, and the shape of liquid starts to deform from the shape caused by surface tension alone. Under a high voltage, the effect of the electric field becomes more prominent until a cone shape begins to form with convex sides and a rounded tip (a Taylor cone). When a certain threshold voltage has been reached the slightly rounded tip inverts and emits a jet of liquid. This is called a cone-jet and is the beginning of the electrospray process.

The formation of the cone, and thus the electrospray, is influenced by several factors, including the viscosity and conductivity of the liquid, the applied voltage, the geometry of the electrode and of the electric field, the diameter and shape of the outlet from the bore from which the liquid emerges, the flow rate of the liquid, the humidity and constitution of the surrounding gas medium, the electric potential, geometry, and distance to the nearest counter-electrode surface, and so on.

The electrospray head of FIGS. 1-3 includes an annular cylindrical reservoir 28 whose inner wall 30 defines the surface of the conduit or bore 18 through which liquid flows. The reservoir is formed of a silicone body filled with a liquid having a coefficient of thermal expansion suitable to expand the flexible inner wall 30 (as shown by dotted line 32) to a sufficient degree to control the exit diameter from the conduit, and also the flow rate through the conduit.

An example of a suitable liquid is one of the family of perfluorinated liquids sold by 3M under the trade mark Fluorinert. For example, the product sold as Fluorinert-70 has a coefficient of thermal expansion of 0.001 per degree centigrade (at 25 degrees centigrade) and is suitable for use as a thermally expanding fluid.

Other candidate fluids (with coefficient of thermal expansion indicated in parentheses) include:

Gasoline (0.000950 per degree centigrade)
Ethanol (0.000750 per degree centigrade)
Water (0.000207 per degree centigrade)
Mercury (0.000182 per degree centigrade)

The silicone material of the reservoir walls has a coefficient of thermal expansion of 0.0009 per degree centigrade, and is thus well matched with the Fluorinert liquid. (This also suggests that a solid silicon block could be employed, though this would suffer from a significant lag and from uneven heating—the Fluorinert, being used primarily as a coolant for electronics, promotes rapid equalization of temperature and thus more rapid response of the reservoir to applied temperature changes.

As an example, a suitable reservoir may have the following dimensions:

Inner diameter of reservoir (at 20 degrees C.): 300 microns
Outer diameter of reservoir: 4.54 mm
Height of cylinder: 10 mm
Wall thickness at inside diameter: 100 microns Thus, at 20 degrees centigrade, the inner diameter of this reservoir is 300 microns. When heat is applied, the volumetric expansion of the reservoir is confined from the exterior and from below by the solid body of borosilicate, and is confined from above by virtue of the top wall being thicker and more rigid than the inner wall 30. Accordingly, the inner diameter is constricted as the reservoir expands, and the following results are seen:

TABLE 1 diameter of orifice as a function of temperature

| Orifice Diameter (microns) | Temperature (degrees C.) |
|---|---|
| 300 | 20.0 |
| 290 | 22.4 |
| 280 | 24.7 |
| 250 | 31.0 |
| 200 | 39.8 |
| 150 | 47.0 |
| 100 | 53.1 |
| 50 | 58.2 |

There are two important points to note from Table 1. The first is that the relationship is close to linear, so that extrapolation and calibration is easily achievable. The second point to note is that a large range of orifice diameters is achievable with only a modest increase in temperature.

Referring back to FIG. 3, the temperature is varied by means of a number of resistors 34 which are energised by a suitable power supply 36. As seen from FIG. 1, the resistors are distributed circumferentially around the outside of the reservoir 28 at equal intervals.

Figure 1:
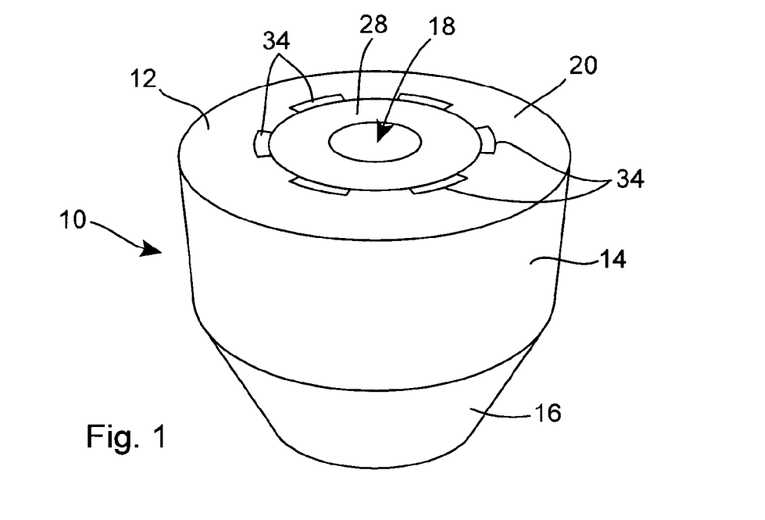
Figure 2:
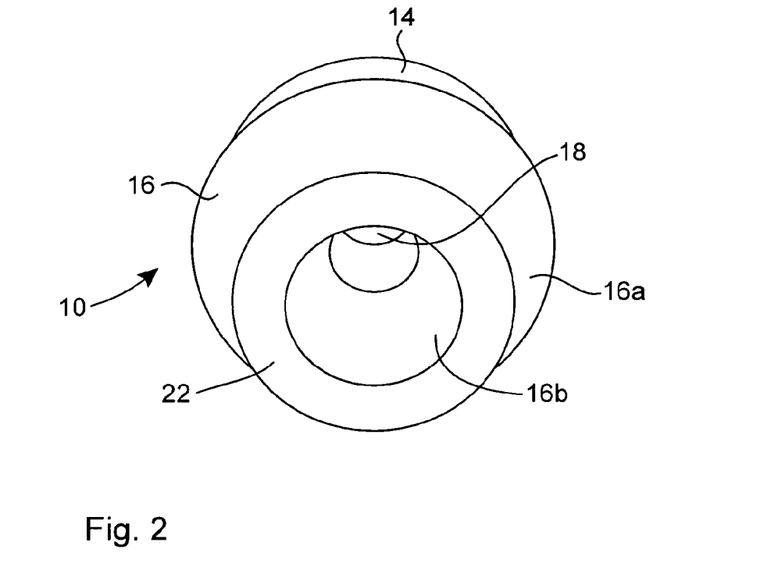
Figure 3:
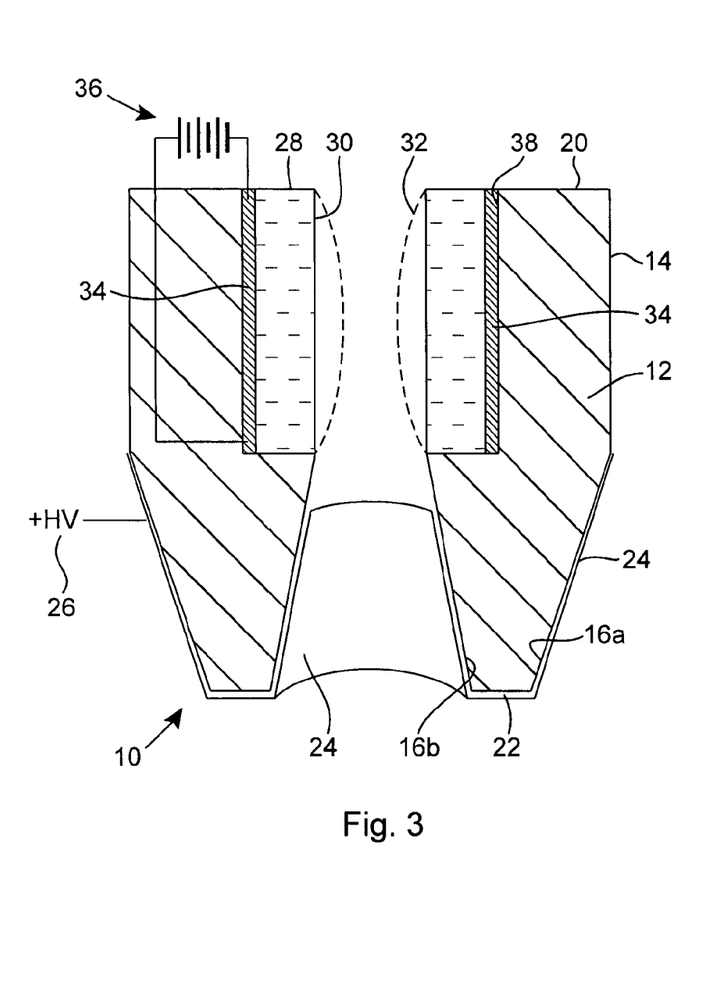

The resistors 34 are shown as having a significant thickness in FIGS. 1 and 3, and are accommodated in a series of cavities which are fabricated into the surface of the cylindrical seating 38 which seats the reservoir 28. In practice, the resistors may be deposited as thin film resistors on the surface 38 of the cylindrical seating before the reservoir has been inserted.

Typically, a thermometer (not shown) such as a platinum resistance thermometer, for example, will be provided in the reservoir or in contact with the reservoir to monitor the temperature (and by extrapolation, indicate the orifice diameter. Suitable control circuitry is used to adjust the power supply to the resistors to maintain the reservoir at the correct temperature for the desired orifice diameter.

More sophisticated control circuitry can be provided which is programmable to apply the correct temperature (or temperature cycle) for a given liquid to be sprayed. Thus, if it is desired to spray a variety of liquids through an electrospraying device, the electrospray head of FIGS. 1-3 may provide the user with the ability to employ a single electrospray head with a controllable orifice output diameter, where conventional electrospraying devices would have required changing the head or capillary tube for the different liquids to be successfully sprayed.

FIG. 4 shows an alternative electrospray head, having a hollow body 50 tapering towards an outlet tip 52. The body may be made of a dielectric material such as glass or plastic. A conductive coating 54 on the exterior surface of the tapering body provides an electrode for application of a high voltage electric field, to create an electrospray of liquid emerging from the tip 52.

On the interior of the tapering body, a plurality of thin film resistors 56 have been deposited at intervals around the circumference of the inner surface, to provide a means for controllably applying heat when energised by a suitable power source and control circuitry (not shown).

Inwardly of the resistors, a reservoir 58 having silicone walls and being filled with Fluorinert-70, is held in place by a bulkhead 60 and by the shape of the tapering tip. The inner wall 62 of the reservoir 58 thus forms a part of a conduit leading from an inlet to the body (not shown, but liquid coming from the inlet travels in the direction indicated by arrow 64), to the outlet tip 52.

Thus, when the resistors 56 are heated, the reservoir undergoes thermal expansion in the only available direction, i.e. inwardly. This causes the inner wall 62 to bulge inwardly, as indicated by the dotted lines 66, thereby constricting the conduit at a point adjacent to the outlet thereof.

FIG. 5 shows a schematic diagram of an apparatus for electrospraying a liquid, in the form of a bronchoscope 70, the form and function of which is generally known. Bronchoscopes allow the passage of instruments into the bronchial passages under the control of a surgeon or operative, and are controllable by manipulative controls (not shown) under the guidance of cameras typically provided towards the distal end 72 of the scope.

The bronchoscope is equipped with an electrospray head 74 as described herein. The electrospray head is directed laterally so that a spray 76 may be directed at a wall 78 of the bronchial passages.

The bronchoscope is supplied with a liquid supply from a reservoir 80 and pump 82, whereby liquid can be supplied at an appropriate flow rate to the electrospray head 74. The liquid will preferably contain an active ingredient, and particularly of interest are liquids including but not limited to:

Therapeutic Biological Molecules

DNA-based

RNA-based protein-based (including, but not limited to: small peptides, proteins, antibodies, growth factors, vaccines)

lipid-based carbohydrate-based

Therapeutic Non-Biological Molecules chemical molecules radio-isotopes chemotherapeutic molecules Diagnostic Molecules labelled/detectable molecules (including, but not limited to: radio-labels)

metal particles which can be accelerated into the cells of the tissue wall 78 to thereby transfect the cells.

Control of the electrospray is effected not by a variable high voltage supply 84 and by the low voltage controllable power supply 86 which feeds the heating resistors of the electrospray head.

Additional control means may be included (not shown) including in particular motors to direct the electrospray head, and directional electrodes to deflect, disperse or concentrate the charged electrospray as desired.

FIG. 6 shows a laboratory or industrial system for delivering an electrospray in vitro. Again this system is shown in highly schematic form for clarity.

An electrospray head 90 is mounted on a micromanipulator 92 which controls the precise position of the head 90 along the X-, Y- and Z-axes. Liquid is supplied to the conduit in the head 90 from a syringe driver 94 under the control of a computer 96.

In another embodiment the liquid may be present in a reservoir close to the head 90 and the liquid flow to the head supplied via an peristaltic action pump between the reservoir and the head.

High voltage power is supplied from a HV power supply 98 to the HV electrode on the electrospray head, the HV power supply similarly being controlled by the computer 96. The low voltage power supply feeding the heating resistors is omitted for clarity, but again the temperature is controllable by the computer, which may be programmed with parameters for spraying different liquids, or which may operate in a learning mode to empirically determine the optimum parameters for a given liquid to be sprayed.

Directional electrodes 100 are positioned to control the direction and shape of the electrospray emerging from the head 90, with this spray being directed to a sample area 102 mounted over a counter-electrode 104. The sample area may be an array of sample cells, each containing an isolated sample, such that the micromanipulator and directional electrodes are operable to control the delivery of liquid to individual sample cells in the array.

A micro-ammeter 106 or other charge/current detector is provided to enable the computer control program to monitor the quantity of charge delivered to the sample area, and thus by inference, the dosage of liquid being delivered over time to individual areas of the sample array where there is a monotonic relationship between the charge collected at the target and the liquid dosage delivered to the target.

Using this apparatus, it is possible to transfect biological samples with DNA or with other biologically active agents in a controlled manner.

Figure 4:
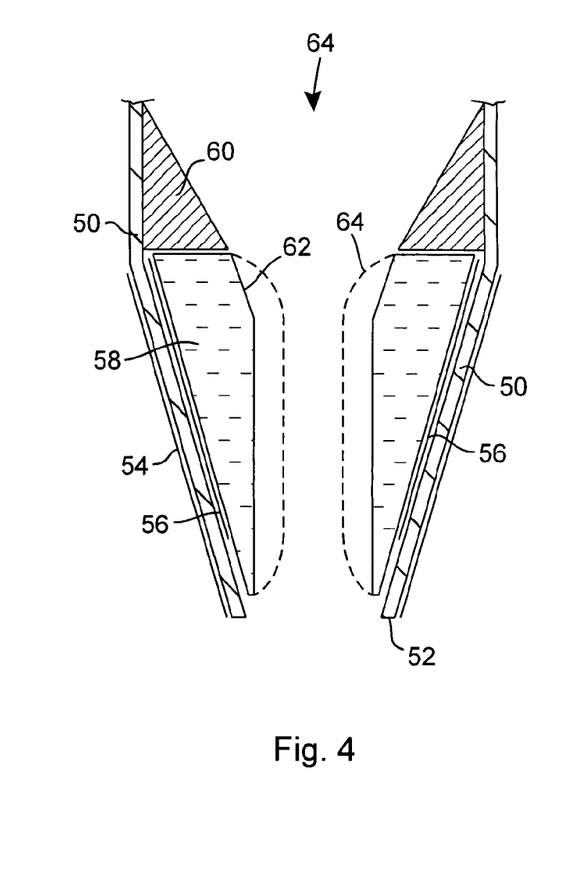
Figure 5:
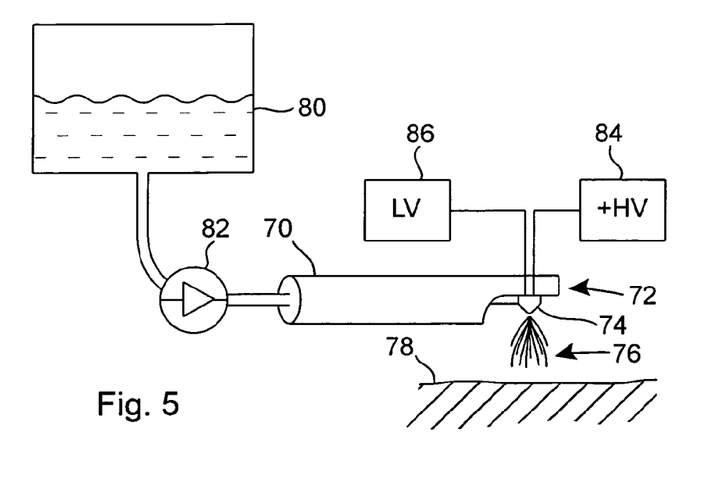
Figure 6:
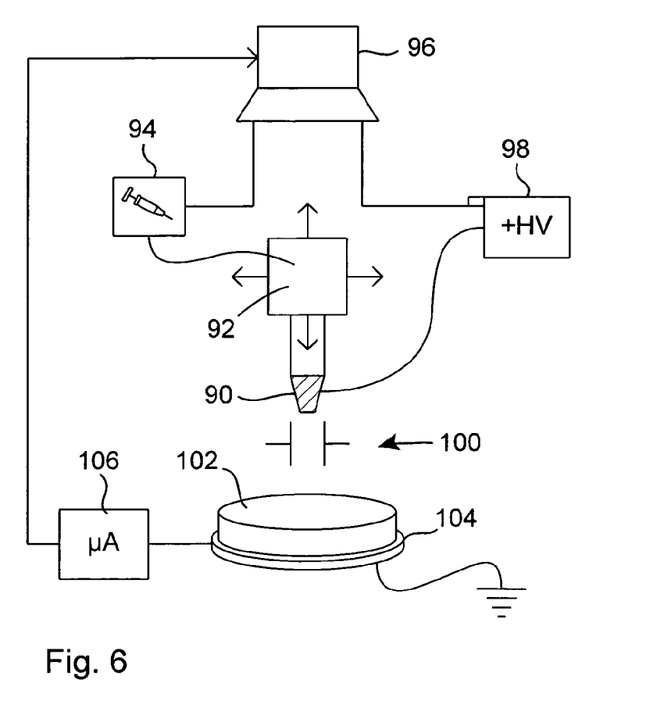
Figure 7:
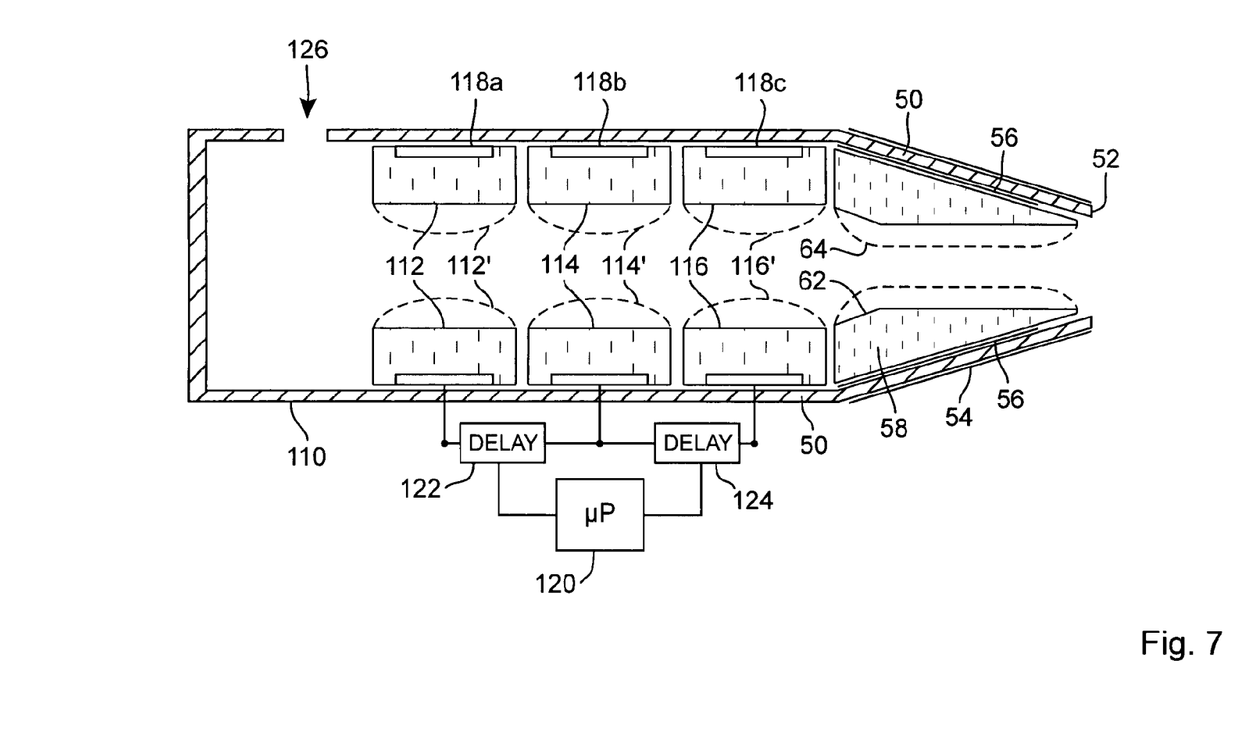

FIG. 7 shows an electrospray device which is based on the spray head of FIG. 4. Like parts are designated with like reference numerals, and the spray tip operates just as previously described.

The device of FIG. 7 has a delivery barrel 110 which is continuous with the hollow body portion 50 leading to the spray head. A plurality of cylindrical peristalsis reservoirs 112,114,116 are arranged in series along the interior of the barrel 110. These peristalsis reservoirs are each provided with a respective annular heating electrode 118a,118b,118c so that they can be controllably heated and thereby expanded to constrict the internal volume defined by the respective cylinders as shown in dotted outline at 112', 114', 116'.

Control of the heating electrodes 118a, 118b, 118c is carried out by a microprocessor 120 which is programmed to implement a delay function (indicated schematically as 122, 124 between the heating of each successive electrode 118a, 118b,118c in series. In this way a peristaltic action is generated along the interior volume defined within the cylindrical peristaltic reservoirs 112,114,116, to assist in pumping fluid from a supply reservoir (not shown) as indicated by arrow 126.

It will be appreciated that in reality the number and arrangement of peristaltic reservoirs can be varied and in practice a greater number than three such reservoirs will be used. If the peristaltic action is sufficiently powerful, having regard to the required delivery rate of fluid through the electrospray head, the viscosity of the fluid, and so on, then a pressurised fluid supply may be dispensed with and the peristaltic action alone can be used to control the rate of delivery of fluid to the spray head.

It will also be appreciated that the reservoir 62 at the spray head itself can be operated as part of the chain of peristaltic reservoirs or can be operated independently to choke the fluid supply and thereby control delivery rate.

Figure 8:
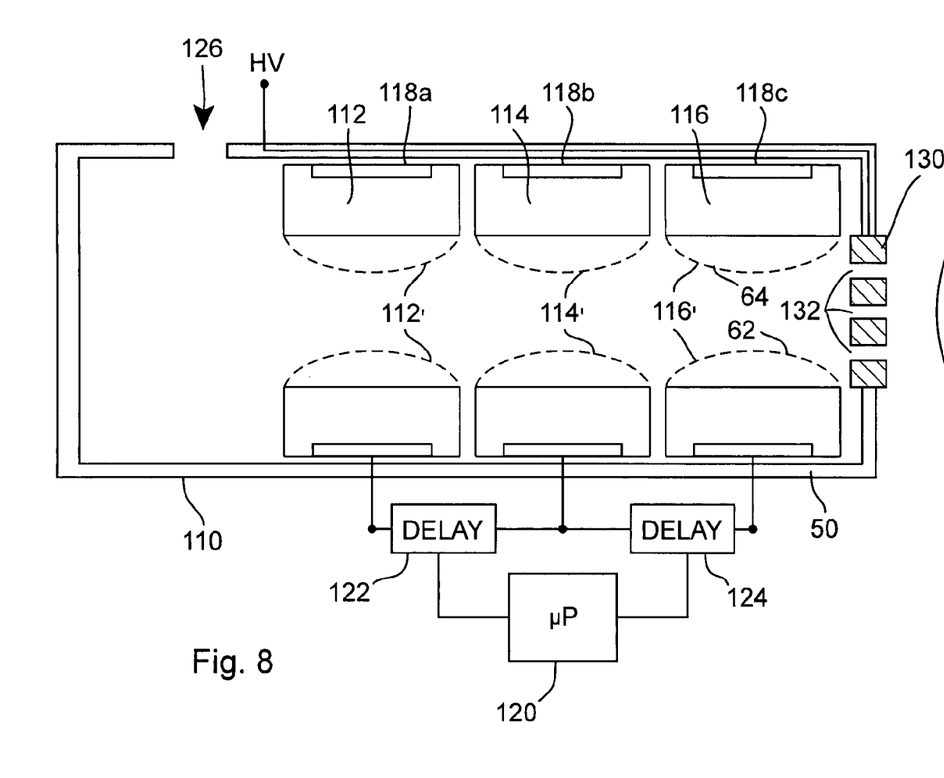

FIG. 8 shows a further alternative embodiment which is similar to that of FIG. 7 in terms of having a plurality of peristalsis reservoirs for pumping or controlling the flow of fluid from a supply 126 through a barrel 110. The same reference numerals have been used to designate those parts having the same function as in FIG. 7.

The spray head 130 of FIG. 8 is different in that it comprises multiple orifices 132 each spraying the fluid to be delivered in parallel directions. Such a spray head can readily be fabricated using MEMS techniques.

Figure 9:
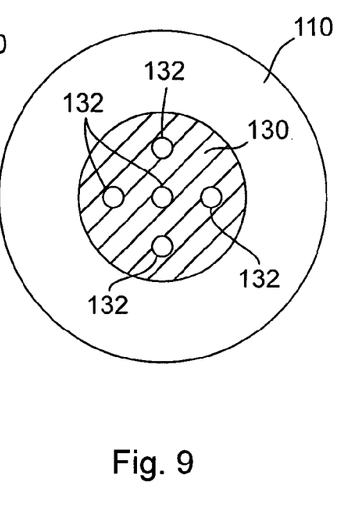

FIG. 9 shows the device of FIG. 8 in end elevation looking towards the spray head.

Figure 10:
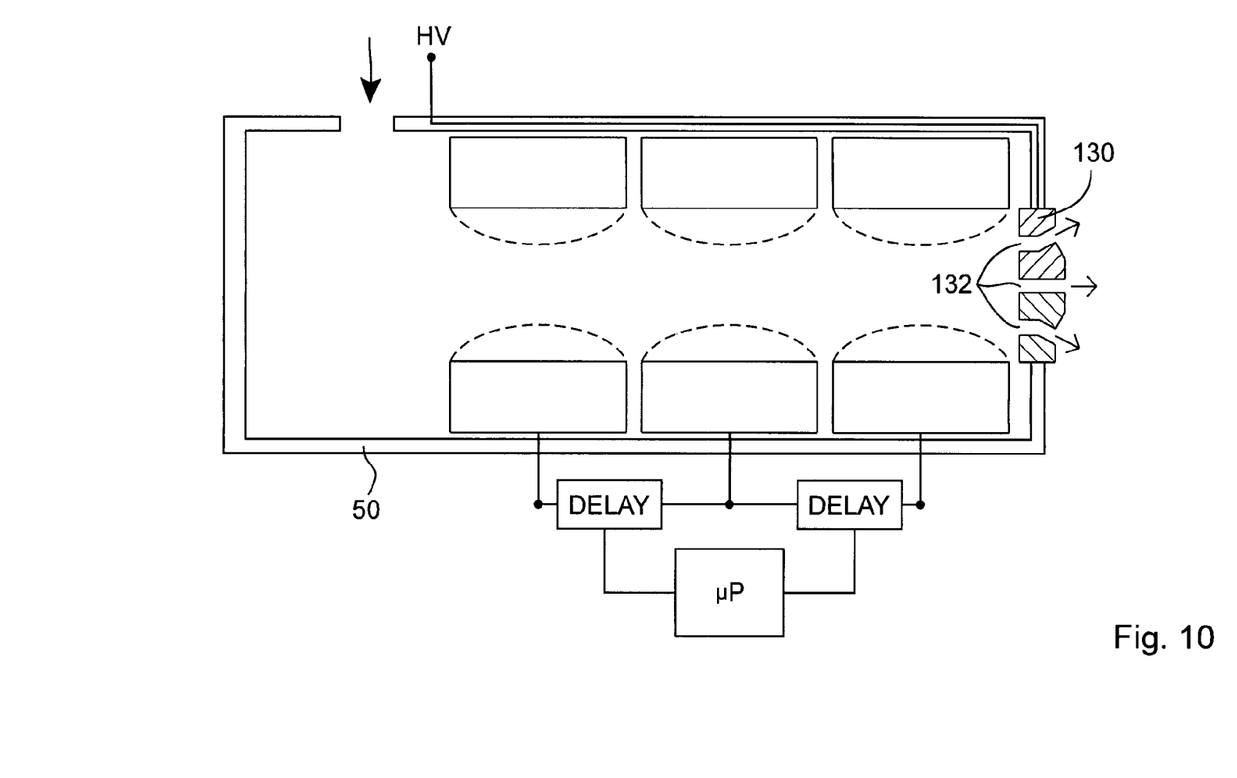

FIG. 10 shows a device which is identical to that of FIGS. 8 and 9 except that the multiple orifices 132 are not parallel but instead diverge from one another to spray the fluid in a divergent spray formation from the spray head.

It will be appreciated that spray heads having multiple orifices such as the spray heads 130 of FIGS. 8-10, need not be used with the peristaltic pumping system shown in FIGS. 8 and 10, and such spray heads can equally be incorporated in devices which do not have such a peristaltic mechanism (such as the device of FIG. 1).

It will also be understood that the five orifices shown in FIGS. 8-10 are illustrative only and the actual number may be any number from a single orifice upwards.

The invention is not limited to the embodiments herein which may be modified or varied without departing from the scope of the claimed invention.

The invention claimed is:

1. An electrospray head for use in an electrospraying apparatus, the electrospray head comprising:
   a body;
   an actuator disposed in said body;
   an internal surface in said body defining a conduit, said conduit having an inlet for receiving a fluid to be sprayed and an outlet for emitting said fluid; and
   a movable wall forming a portion of said internal surface defining the conduit;
   wherein said movable wall is arranged to co-operate with said actuator to constrict or dilate said conduit upon operation of the actuator;
   wherein the movable wall is located adjacent the outlet of the conduit whereby the effective exit dimensions of the conduit can be varied by controlling the actuator;
   wherein the actuator comprises an expandable member disposed adjacent said movable wall, and means for varying the expansion of said expandable member;
   whereby the effective exit dimensions of the conduit can be varied by controlling the actuator to provide an additional element of control to affect the fluid dynamics and the creation of an electrospray plume.

2. An electrospray head according to claim 1, wherein the movable wall comprises a cylindrical wall section whose diameter can be varied by controlling the actuator.

3. An electrospray head according to claim 2, wherein said cylindrical wall section extends around the entire circumference of a cylinder.

4. An electrospray head according to claim 2, wherein said cylindrical wall section extends around a sector of the circumference of a cylinder.

5. An electrospray head according to claim 2, wherein said actuator is disposed circumferentially outside said cylindrical wall section.

6. An electrospray head according to claim 5, wherein said actuator is a generally cylindrical actuator operable to compress said cylindrical wall section and thereby constrict the diameter thereof.

7. An electrospray head as claimed in claim 6, wherein said expandable member comprises a fluid reservoir which may be caused to expand.

8. An electrospray head as claimed in claim 7, wherein said movable wall comprises a boundary of said reservoir.

9. An electrospray head as claimed in claim 7, wherein said fluid reservoir is constrained from movement in at least one direction, whereby the expansion of the fluid reservoir is enhanced in a different direction.

10. An electrospray head as claimed in claim 9, wherein said body is a solid structure having a seat within which said fluid reservoir is disposed.

11. An electrospray head as claimed in claim 10, wherein said fluid reservoir is in the form of an annular cylinder having an inner cylindrical face defining said movable wall and an external cylindrical face abutting said seat in which said annular cylindrical reservoir is seated, whereby radial expansion of the reservoir is directed inwardly to constrict said inner cylindrical diameter.

12. An electrospray head as claimed in claim 11, wherein the means for heating comprises a plurality of resistors disposed radially outwardly of the annular cylindrical reservoir.

13. An electrospray head as claimed in claim 12, wherein the plurality of resistors are embedded in the body and flush with the seat.

14. An electrospray head as claimed in claim 6, wherein the expandable member is a thermally expandable structure, and wherein the means for varying the expansion thereof comprises means for heating the thermally expandable structure.

15. An electrospray head as claimed in claim 14, wherein the means for heating comprises at least one resistor.

16. An electrospray head as claimed in claim 1, wherein said movable wall is controllable to simultaneously constrict and dilate different portions of said conduit.

17. An electrospray head as claimed in claim 16, wherein said movable wall is controllable to generate a peristaltic contraction movable along said conduit.

18. An electrospray head as claimed in claim 16, wherein said movable wall comprises a plurality of independently controllable sections which together define said conduit, and each independently controllable section being arranged to co-operate with an actuator to constrict or dilate a portion of said conduit upon operation of the actuator.

19. An electrospray head as claimed in claim 1, wherein said outlet of said conduit comprises a plurality of outlet orifices.

20. An electrospray head as claimed in claim 19, wherein said plurality of outlet orifices are configured to direct fluid emerging therefrom in a plurality of different directions.

21. An electrospray head as claimed in claim 1, further comprising an electrode adapted to energize said fluid with a high voltage when connected to an appropriate power supply.

22. An electrospray head as claimed in claim 21, further comprising an electrical circuit for supplying said electrode with a high voltage.

23. An electrospray head as claimed in claim 1, wherein said body comprises a solid body structure having fabricated therein: said conduit; a space for receiving said movable wall; and a space for receiving said actuator.

24. An electrospray head as claimed in claim 23, wherein said solid body structure is selected from a substrate of borosilicate, quartz, or silicon.

25. An electrospraying device comprising an electrospray head, and means for receiving a supply of fluid for electrospraying, wherein said electrospray head comprises:
a body;
an actuator disposed in said body;
an internal surface in said body defining a conduit, said conduit having an inlet for receiving a fluid to be sprayed and an outlet for emitting said fluid; and
a movable wall forming a portion of said internal surface defining the conduit;
wherein said movable wall is arranged to co-operate with said actuator to constrict or dilate said conduit upon operation of the actuator,
wherein the movable wall is located adjacent the outlet of the conduit whereby the effective exit dimensions of the conduit can be varied by controlling the actuator;
wherein the actuator comprises an expandable member disposed adjacent said movable wall, and means for varying the expansion of said expandable member;
whereby the effective exit dimensions of the conduit can be varied by controlling the actuator to provide an additional element of control to affect the fluid dynamics and the creation of an electrospray plume.

26. A bronchoscope apparatus comprising an electrospraying device mounted on a body adapted for insertion into the respiratory passages of a subject,
wherein said electrospraying device comprises an electrospray head, and means for receiving a supply of fluid for electrospraying, wherein said electrospray head comprises:

a body;

an actuator disposed in said body;

an internal surface in said body defining a conduit, said conduit having an inlet for receiving a fluid to be sprayed and an outlet for emitting said fluid; and a movable wall forming a portion of said internal surface defining the conduit;

wherein said movable wall is arranged to co-operate with said actuator to constrict or dilate said conduit upon operation of the actuator;

wherein the movable wall is located adjacent the outlet of the conduit whereby the effective exit dimensions of the conduit can be varied by controlling the actuator;

wherein the actuator comprises an expandable member disposed adjacent said movable wall, and means for varying the expansion of said expandable member;

whereby the effective exit dimensions of the conduit can be varied by controlling the actuator to provide an additional element of control to affect the fluid dynamics and the creation of an electrospray plume;

whereby the electrospray head of the device may be directed at a tissue wall for delivery of an agent to said tissue by electrospraying.

27. An apparatus for delivering a biological agent to a sample of cells in vitro, comprising a sample area for receiving said sample of cells, and an electrospraying device, wherein said electrospraying device comprises an electrospray head, and means for receiving a supply of fluid for electrospraying, wherein said electrospray head comprises:

a body;

an actuator disposed in said body;

an internal surface in said body defining a conduit, said conduit having an inlet for receiving a fluid to be sprayed and an outlet for emitting said fluid; and a movable wall forming a portion of said internal surface defining the conduit;

wherein said movable wall is arranged to co-operate with said actuator to constrict or dilate said conduit upon operation of the actuator;

wherein the movable wall is located adjacent the outlet of the conduit whereby the effective exit dimensions of the conduit can be varied by controlling the actuator;

wherein the actuator comprises an expandable member disposed adjacent said movable wall, and means for varying the expansion of said expandable member;

whereby the effective exit dimensions of the conduit can be varied by controlling the actuator to provide an additional element of control to affect the fluid dynamics and the creation of an electrospray plume;

the electrospray head of said electrospraying device being positioned to deliver said biological agent from said supply of fluid to said sample of cells by electrospraying, and optionally, a counter-electrode positioned relative to the sample area to direct said electrospray.

28. A method of treatment of the human or animal body comprising the steps of: (a) providing an apparatus having an electrospray head, the electrospray head comprising:

a body;

an actuator disposed in said body;

an internal surface in said body defining a conduit, said conduit having an inlet for receiving a fluid to be sprayed and an outlet for emitting said fluid; and a movable wall forming a portion of said internal surface defining the conduit;

wherein said movable wall is arranged to co-operate with said actuator to constrict or dilate said conduit upon operation of the actuator;

wherein the movable wall is located adjacent the outlet of the conduit whereby the effective exit dimensions of the conduit can be varied by controlling the actuator;

wherein the actuator comprises an expandable member disposed adjacent said movable wall, and means for varying the expansion of said expandable member;

whereby the effective exit dimensions of the conduit can be varied by controlling the actuator to provide an additional element of control to affect the fluid dynamics and the creation of an electrospray plume;

and (b) operating said apparatus to deliver an electrospray agent to said human or animal body.

* * * * *